(12) United States Patent
Sharman et al.

(10) Patent No.: US 10,702,205 B2
(45) Date of Patent: Jul. 7, 2020

(54) APPARATUS AND METHOD FOR MONITORING REHABILITATION FROM SURGERY

(71) Applicant: Claris Healthcare Inc., Vancouver, BC (CA)

(72) Inventors: Paul Sharman, Vancouver (CA); Geof Auchinleck, Vancouver (CA)

(73) Assignee: Claris Healthcare Inc., Vancouver, BC (CA)

( * ) Notice: Subject to any disclaimer, the term of this patent is extended or adjusted under 35 U.S.C. 154(b) by 152 days.

(21) Appl. No.: 16/027,298

(22) Filed: Jul. 4, 2018

(65) Prior Publication Data

US 2018/0317836 A1 Nov. 8, 2018

Related U.S. Application Data

(63) Continuation of application No. 15/193,259, filed on Jun. 27, 2016, now abandoned.

(51) Int. Cl.
  *A61B 5/00* (2006.01)
  *G06F 19/00* (2018.01)
  (Continued)

(52) U.S. Cl.
  CPC .............. *A61B 5/4528* (2013.01); *A61B 5/01* (2013.01); *A61B 5/1072* (2013.01); *A61B 5/1075* (2013.01); *A61B 5/1118* (2013.01); *A61B 5/1121* (2013.01); *A61B 5/4585* (2013.01); *A61B 5/4824* (2013.01); *A61B 5/4833* (2013.01); *A61B 5/4848* (2013.01); *A61B 5/7278* (2013.01); *A61B 5/742* (2013.01); *A61B 5/7475* (2013.01); *G06F 19/00* (2013.01); *G06F 19/3418* (2013.01); *G06F 19/3481* (2013.01);
  (Continued)

(58) Field of Classification Search
  None
  See application file for complete search history.

(56) References Cited

U.S. PATENT DOCUMENTS 6,963,772 B2 * 11/2005 Bloom ..................... A61B 5/01
                                                          600/547
2013/0217998 A1 * 8/2013 Mahfouz ................ G16H 50/50
                                                          600/409
(Continued)

*Primary Examiner* — Brian T Gedeon
(74) *Attorney, Agent, or Firm* — Hancock Hughey LLP

(57) ABSTRACT

Apparatus and methods are described for setting rehabilitation goals for a patient, measuring patient movements, storing the movement data for later transfer to a computer, displaying progress indicators and inspirational messages based on progress towards goals, reporting movement, skin temperature and swelling data to a caregiver so that they monitor compliance and be aware of potential infection. The invention consolidates data from motion, temperature and swelling sensors placed on the patient with data received directly from the patient in response to questions displayed on a tablet computer screen, to create one or more representative values indicating the patient's current status. These representative values may include the patient's degree of compliance with their prescribed exercise and icing regimen; their degree of wellness based on their self-reported pain scale and sensed temperature and limb swelling; and their current level of physical activity as detected by the motion sensors.

20 Claims, 7 Drawing Sheets

(51) Int. Cl.
*G16H 10/60* (2018.01)
*A61B 5/11* (2006.01)
*A61B 5/107* (2006.01)
*A61B 5/01* (2006.01)
*G16H 40/63* (2018.01)
*G16H 20/30* (2018.01)

(52) U.S. Cl.
CPC .............. *G16H 10/60* (2018.01); *G16H 20/30* (2018.01); *G16H 40/63* (2018.01); *A61B 5/002* (2013.01); *A61B 5/725* (2013.01); *A61B 2505/09* (2013.01); *A61B 2562/0261* (2013.01); *A61B 2562/222* (2013.01)

(56) References Cited

U.S. PATENT DOCUMENTS

| | | | | |
|---|---|---|---|---|
| 2014/0296749 | A1* | 10/2014 | Reid, Jr. .............. | A61B 5/6812 600/587 |
| 2015/0045700 | A1* | 2/2015 | Cavanagh ............ | A61B 5/4528 600/595 |
| 2016/0302721 | A1* | 10/2016 | Wiedenhoefer ...... | A61B 5/4528 |
| 2016/0324461 | A1* | 11/2016 | Hallberg .............. | A61B 5/4528 |

\* cited by examiner

APPARATUS AND METHOD FOR MONITORING REHABILITATION FROM SURGERY

FIELD OF THE INVENTION

The present invention relates to apparatus and methods for monitoring a patient in various respects including the compliance of a patient to the rehabilitation regimen that is prescribed for preparation for and recovery from joint surgery such as total joint arthroplasty. More specifically, the present invention relates to the use of sensors applied to a post-surgical patient for the purpose of detecting, acquiring and measuring the patient's movement, temperature and limb circumference and for using acquired data for tracking the patient's progress during rehabilitation while reporting their progress to their caregivers.

Joint arthroplasty is a surgical procedure for resurfacing or replacing those parts of knee, hip, elbow, shoulder and other joints that are damaged, typically from arthritis, in older adults. Knee arthroplasty is a very common procedure—more than 700,000 were done in the United States in 2015—and is rapidly increasing as a result of an aging population.

A key factor in the success of a joint arthroplasty is the compliance of the patient with the required rehabilitation regimen. This regimen may begin prior to surgery—certain exercises and stretches are sometimes prescribed in advance of surgery to improve the chances of success—and is certainly required for some months after the surgery is complete. Rehabilitation may include such activities as flexing the affected joint through a certain range of motion, applying ice or heat to the joint, and monitoring the surgical site for signs of infection, excessive swelling or drainage.

Rehabilitation is usually managed by a physiotherapist or other medical professional who instructs the patient in a clinical setting, then checks with the patient occasionally to monitor their progress. This means that the patient is expected to be self-motivated to follow the required regimen and accurately report to the caregiver their level of compliance. Many find this difficult to do and may not be entirely honest about their level of compliance. As a caregiver may be responsible for a large number of patients, it may be difficult for them to determine which patients are complying well and which need additional attention.

To encourage better compliance, it would be advantageous to provide a patient with timely feedback and encouragement as to their progress, and to provide quantitative measurements as to their progress, both to the patient and their caregivers.

Three kinds of measurements can provide information of value. The first is measurement of the number of flexions, degree of flexion and maximum and minimum amount of flexion of the affected joint; the second is measurement of the skin temperature near the surgical site; and the third is the degree of swelling of the limb. The number and the degree of flexions including the maximum and minimum flex angles is indicative of the patient's activity level and progress towards re-establishing a full range of motion. The temperature near the wound site can provide an early indication of infection as it has been known since Roman times that wound infection is indicated by the four factors of calor, dolor, rubor and tumor—heat, pain, redness and swelling. Further, icing of the wound site after surgery is indicated for improved recovery, therefore measuring the amount and duration of temperature decrease near the wound site is indicative of the patient's compliance with prescribed icing techniques. Similarly, increased swelling of the limb near the surgical site may be indicative of infection, overuse of the limb or a need for additional icing.

Using electronic sensors to measure joint flexion has been demonstrated in the laboratory. Several published papers show the use of integrated circuit accelerometers or capacitive, resistive or inductive flex sensors to detect joint movements and range of motion. Similarly, there are many well-known ways to measure skin temperature using electronic and mechanical thermometers. Measurement of swelling is typically done manually, using a tape measure or similar device to measure limb circumference near the surgical site.

Existing devices for measuring joint motion and temperature require separate sensors connected to a computer for collecting data for interpretation by a caregiver. These systems do not provide a convenient single unit for measuring the required parameters, nor do they provide for storage of the data for later transmission to a caregiver's computer. In addition, a single temperature sensor near the wound site may provide misleading data if the patient moves into a hot or cold environment, as there is no way, with one sensor, to tell if the temperature increase or decrease is a local effect (caused by infection or icing of the joint). Manual measurement of swelling provides only intermittent data and may be inaccurate as a result of varying measurement locations and measurement techniques.

The prior art fails to teach the combination of data from motion and temperature sensors into a patient coaching system and caregiver management system. Such a system can be used by a caregiver to set specific goals (such as number of repetitions of joint flexion, target ranges of motion or target temperature and duration during icing) and to provide the patient with feedback and encouragement as to achievement of those goals based on measurements by the sensors.

The prior art also fails to teach consolidating data from patient-worn sensors and patient reported data into one or more figures of merit which allow a caregiver to easily determine if the patient is doing well or not.

SUMMARY OF THE INVENTION

The current invention describes apparatus and method for setting rehabilitation goals for a patient, measuring their movements, storing the movement data for later transfer to a computer, displaying progress indicators and inspirational messages based on progress towards goals, reporting movement, skin temperature and swelling data to a caregiver so that they monitor compliance and be aware of potential infection.

One advantage of the current invention is the use of two temperature sensors to monitor patient skin temperature—one located on the skin near the surgical wound site and another on the skin some distance from the wound site, so that the wound site temperature can be compared to a basal skin temperature, eliminating environmental variations that might effect the temperature measurements.

In another aspect, the sensor apparatus in accordance with the current invention provides for data storages and wireless communications between the sensor apparatus and a computer or computer network, such that readings made by the sensors can be stored within the sensor apparatus, then transmitted wirelessly to a computer or network whenever a wireless connection is available, therefore eliminating the need for the patient to remain within wireless communications range of a computer, without risking loss of measurement data.

In yet another aspect, the current invention consolidates data from motion, temperature and swelling sensors with data received directly from the patient in response to questions displayed on a tablet computer screen, to create one or more representative values indicating the patient's current status. These representative values may include the patient's degree of compliance with their prescribed exercise and icing regimen; their degree of wellness based on their self-reported pain scale and sensed temperature and limb swelling; and their current level of physical activity as detected by the motion sensors.

BRIEF DESCRIPTION OF THE DRAWINGS

These and other objects, features and advantages of the present invention will become apparent upon reference to the following detailed description of the exemplary embodiment presented herein and to the drawings wherein.

DETAILED DESCRIPTION OF THE INVENTION AND ILLUSTRATED EMBODIMENTS

Figure 1:
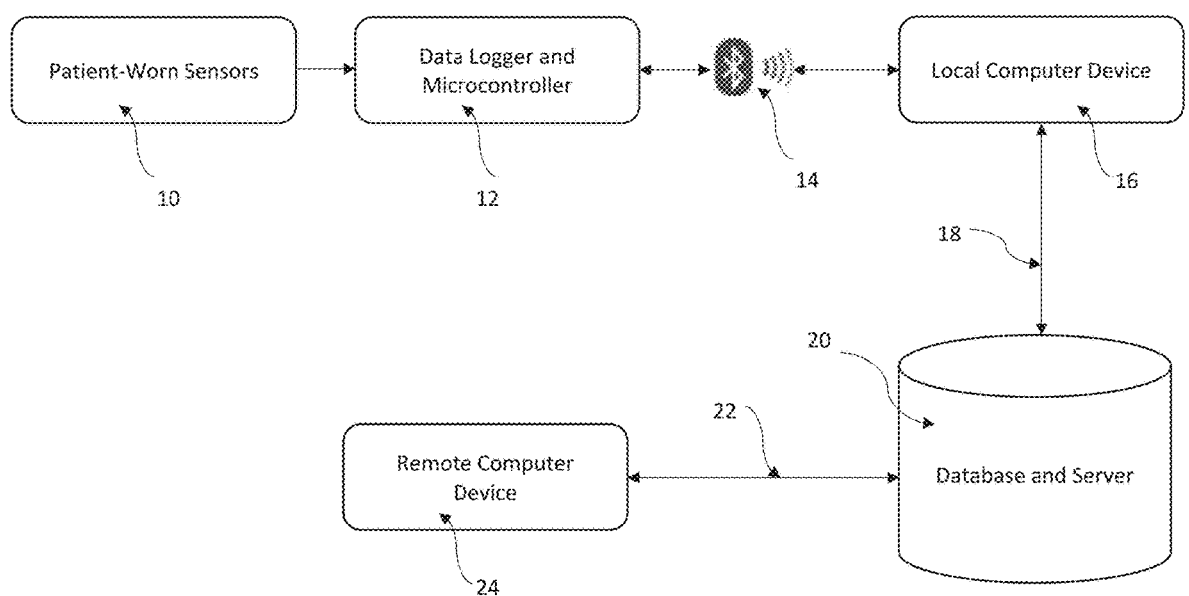
FIG. 1 is a block diagram of an apparatus according to the invention.

FIG. 1 illustrates the major functional components of the preferred embodiment according to the invention. Patient-worn sensors 10 are connected to data logger and microcontroller 12, both of which are described more fully hereinafter, such that the microcontroller can cause data to be read from sensors 10 and stored in memory. At pre-determined intervals, microcontroller 12 tests to see if a connection to local computer 16 can be made through wireless data connection 14, which in the preferred embodiment is a Bluetooth connection, but may be a WiFi or other data connection. If a connection is available, microcontroller 12 retrieves data from sensors 10 from the memory and sends it across wireless data connection 14 to local computer 16. Local computer 16, which in the preferred embodiment is an Android tablet computer, then transfers the data, using Internet connection 18, to database and server 20, which, in the preferred embodiment is a 'cloud service' such as those provided by Heroku and Amazon.

Also connected to database and server 20 is remote computer 24, via Internet connection 22, which may be any computer capable of running a web browser such as Google Chrome or the like. Thus, it can be seen that through the various devices and connections described, data from sensors 10 can be delivered to database and server 20, from where it can be retrieved by remote computer 24 for viewing and interpretation by a user of remote computer 24.

Note that Internet connections 18 and 22 permit communications in the opposite direction to that described—remote computer 24 can send information via Internet connection 22 to database and server 20, from whence it can be further sent to local computer 16. In this way it is possible for remote computer 24 to cause computer 16 to display messages, images, videos or other information on local computer 16.

Figure 2:
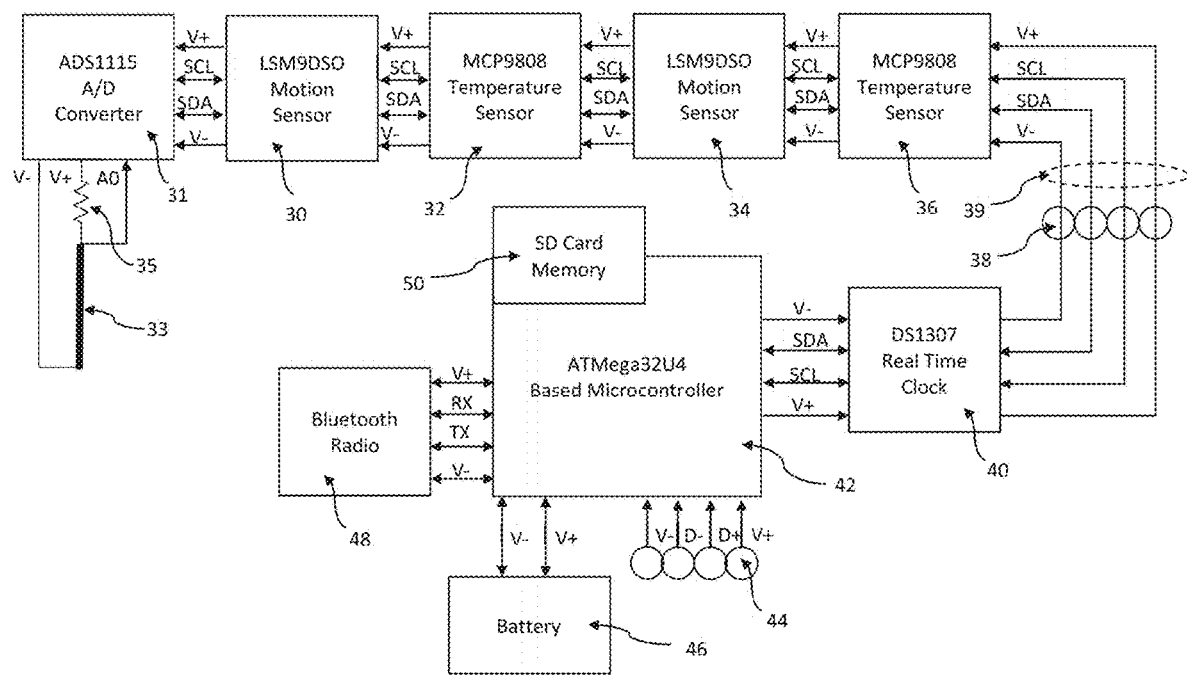
FIG. 2 is a schematic representation of the sensor and data logger components of the apparatus shown in FIG. 1.

FIG. 2 more fully illustrates patient worn sensors 10 and data logger and microcontroller 12. In he preferred embodiment, data logger and microcontroller 12 is made up of ATMega32U4 processor board 42, connected to SD card memory unit 50, which in the preferred embodiment is an Adafruit Feather 32u4 Adalogger (Adafruit Industries LLC, NY, N.Y.). Incorporated into processor board 42 is USB connector 44, serial communications connections, I2C bus connections and battery charging circuitry. Battery 46 is a lithium polymer 3.7 volt 12 mAh battery, which in the preferred embodiment is a PKCell LP503562, which is connected to the battery pins of processor board 42.

Bluetooth radio 48 is embodied with an Adafruit BlueFruit EZ Link module. This module is connected to the auxiliary power supply connections of processor board 42 and to the serial data transmit (TX) and receive (RX) pins of processor board 42.

The remaining modules of data logger and microcontroller 12 and patient worn sensors 10 are connected to processor board 42 using the industry standard I2C bus. This communications bus provides electrical power and digital communications to 100 or more modules connected on the same set of four wires. As each device connected to the I2C bus has a unique digital address, the software running on microcontroller 12 can request and receive data from each module as required.

Real time clock 40 is an I2C module based on the DS1307 real time clock chip. In the preferred embodiment, this is an Adafruit DS1307 Real Time Clock module, which includes a battery backup to ensure that real time clock data is preserved even if battery 46 should become exhausted.

Also connected to the I2C bus are two MCP9808 temperature sensors (Adafruit MCP9808) and two LSM9DS0 motion sensors (Adafruit LSM9DS0). Motion sensor 30 is connected to the distal end of I2C cable 39 so that it may be attached distal to the patient's affected joint as hereinafter described; temperature sensor 32 is connected to the cable 39 some distance proximal to motion sensor 30, such that it may be attached to the patient's skin near the surgical site; and motion sensor 34 and temperature sensor 36, are connected some distance proximal to temperature sensor 32 so that they can be attached to the skin proximal to the patient's affected joint. As detailed below, temperature sensor 32 is attached to the patient near enough to the surgical site that the sensor is capable of measuring increases (or decreases) in temperature at the surgical site, which could be indicative of infection (or icing). Temperature sensor 36 is attached to the patient spaced away from sensor 32 by enough distance that the sensor 36 measures a basal skin temperature that is not effected by an increase or decrease in temperature at the surgical site where the sensor 32 is located.

Also connected to the I2C bus is one ADS1115 analog to digital converter 31 (Adafruit ADS1115). Connected to analog input A0 of analog to digital converter 31 is stretch sensor 33, which in the preferred embodiment is made of a length of 2 mm diameter conductive rubber cord (Adafruit 519). Stretch sensor 33 is connected between 1K ohm pull up resistor 35, which is connected to positive supply voltage V+ and negative supply voltage V−. This produces a voltage at the junction of stretch sensor 33 and resistor 35 that varies in proportion to the extension of stretch sensor 33. This varying voltage is read by analog to digital converter 31 via input connection A0.

Cable 39 connecting real time clock 40 and temperature sensor 36 includes connector 38, which allows the temperatures sensors 32 and 36, motion sensors 30 and 34 and stretch sensor 33 to be disconnected from real time clock 40, thus making the module containing real time clock 40, processor board 42, Bluetooth radio 48, SD card memory 50 and battery 46 separable from the sensor components.

Figure 3:
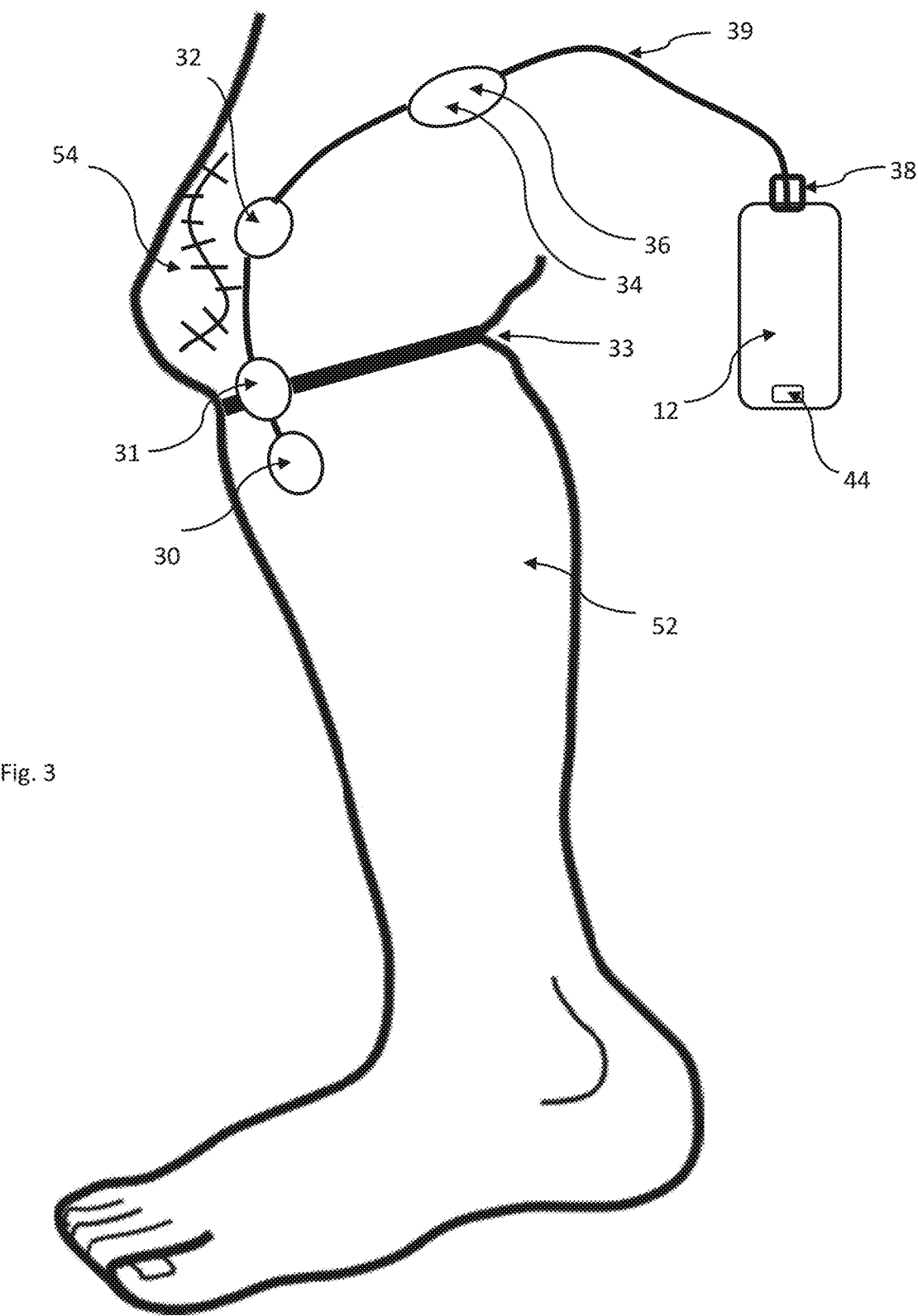
FIG. 3 is a schematic illustration of a post-operative patient's leg illustrating how the sensors, data logger and microcontroller may be applied to the patient's leg.

FIG. 3 shows how patient worn sensors 10 and data logger and microcontroller 12 might be applied to the leg of patient 52 during recovery from knee surgery. Motion sensor 30 is applied to the patient's leg below the knee and may be taped in place, attached to the surgical dressing, or tucked inside an elastic bandage applied to the leg. Analog to digital converter 31 is mounted such that connected stretch sensor 33 may be wrapped around the leg immediately below the knee such that it is normally under slight tension. Similarly, temperature sensor 32 is attached to the leg, but is located a near as practicable to surgical incision 54. In the preferred embodiment, temperature sensor 36 and motion sensor 34 are contained within the same enclosure and are attached to the leg of patient 52 above the knee. All of the sensors are connected with cable 39, which is connected to data logger and microcontroller 12 with connector 38. Microcontroller 12 encloses real time clock 40, processor board 42, SD memory 50, Bluetooth radio 48, battery 46 and USB connector 44. USB connector 44 is accessible such that microcontroller 12 can be plugged into a standard USB cable to recharge battery 46 and to upload programs to processor board 42. In use, microcontroller 12 may be strapped to the leg of patient 52 with an elastic strap, clipped on a belt, or placed in a pocket.

Figure 4:
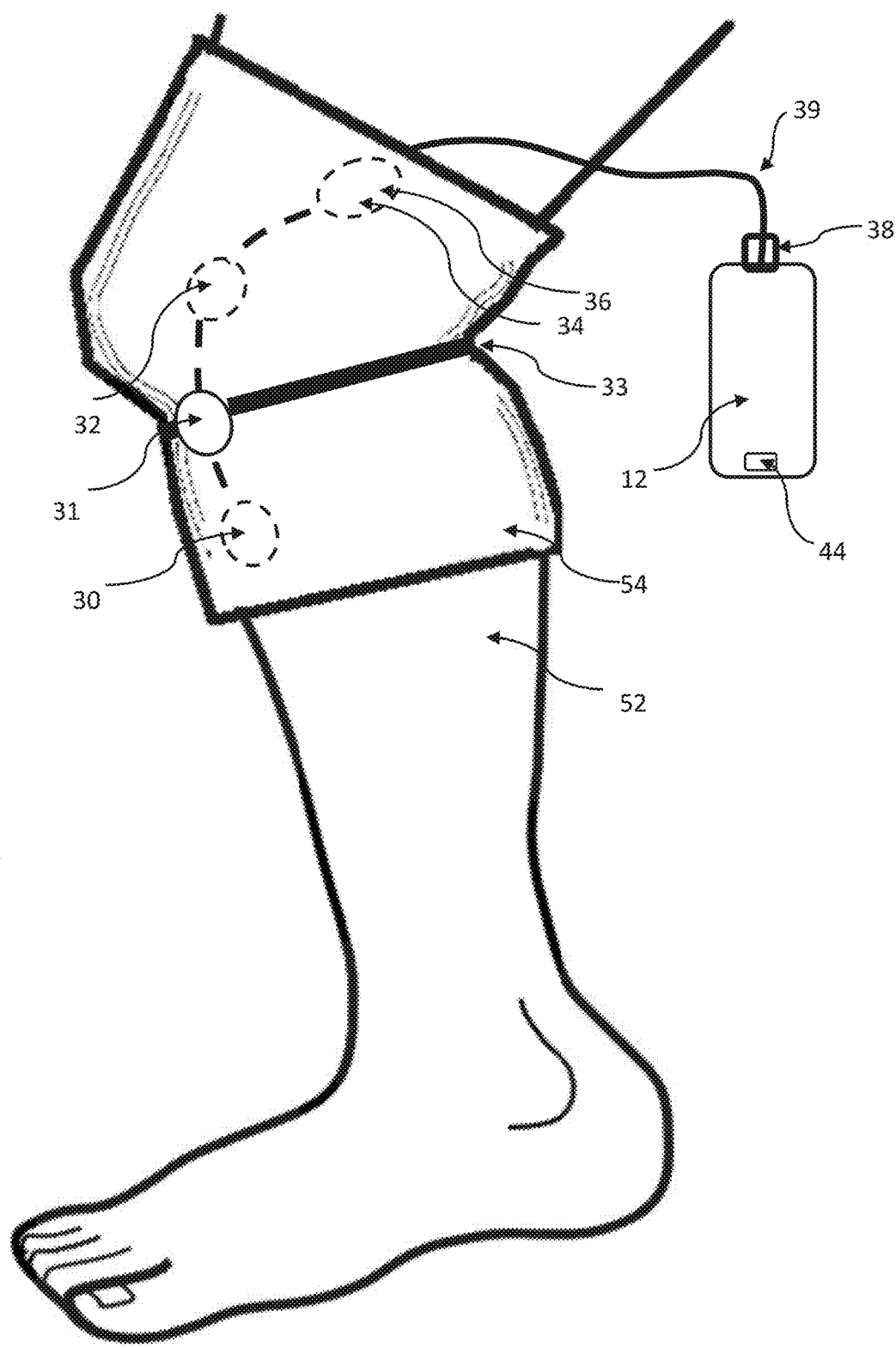
FIG. 4 is a schematic illustration analogous to FIG. 3 except illustrating an alternative embodiment of an apparatus for locating the sensors on the patient's leg.

FIG. 4 shows an alternative means for locating the sensors on a patient's leg in accordance with the invention, as it might be used in rehabilitation from knee surgery. In this embodiment, sensors 30, 32 34 and 36 are fastened inside elastic sleeve 54, while sensor 33 and analog to digital converter 31 are fastened outside elastic sleeve 54 all connected via cable 39. The sensors are pre-positioned at locations inside and outside the sleeve such that when the sleeve is pulled up over the knee, the sensors are located in the desired positions. This has the advantage of simplifying the location and attachment of the sensors to the patient.

In typical use, a caregiver uses remote computer 24, to create a record for a new patient using a web application hosted by database and server 20. As part of this setup, the caregiver assigns local computer 16 to patient 52, creating a link between the record for the patient and local computer 16. The caregiver then pairs patient worn sensors 10 to local computer 16 so that data from patient worn sensors 10 is transmitted to local computer 16 using Bluetooth connection 14 from where it is further transferred to database and server 20 over Internet connection 18, where it is stored in a database record associated with patient 52.

As soon as the connection is made, data logger and microcontroller 12 begins to collect data from patient worn sensors 10 and store it locally in SD card memory 50. In the preferred embodiment, data is collected approximately every 1/10 second. From time to time, microcontroller 12 checks to see if there is a connection to local computer 16 available using Bluetooth connection 14. If so, microcontroller 12 transmits any data not previously transmitted to local computer 16. In turn, local computer 16 transmits the data to database and server 20 over Internet connection 18.

From time to time, the caregiver may choose to review the data collected by patient worn sensors 10. Using a web browser on remote computer 24, the caregiver can retrieve data from database and server 20. The web service running on database and server 20 retrieves the data obtained from patient worn sensors 10 and performs an analysis of the data to extract features from the raw data.

Many different techniques for extracting knee joint angles from accelerometer and gyroscope data are known in the art, many of which can be implemented with the sensors 30 and 34 herein described. For example, a first approximation of the knee joint angle can be determined using only the three-axis accelerometers of sensors 30 and 34. In this implementation, the acceleration due to gravity is detected by each sensor to provide an X, Y and Z acceleration measurement that varies depending on the orientation of the sensor with respect to the ground. As sensor 30 is attached to the shank of patient 52 and sensor 34 is connected to the thigh of patient 52, the X, Y and Z axis readings from each sensor define a vector V that represents the orientation of the sensor on the shank or thigh, and the angle between the two resulting vectors represents the angle between the shank and thigh. The formula for determining the angle between two vectors V1 and V2 is:

$$\theta = \cos^{-1}(V1 \cdot V2)/(|V1| \times |V2|)$$

Where · indicates the dot product of the vectors and |V| indicates the magnitude of the vector.

Measuring only accelerations will give a reasonably accurate representation of knee flexion angle when patient 52 is at rest, but will be less accurate when there is any motion. To improve the estimate of the actual knee angle, there are several different filtering techniques to remove signal noise and accelerations due to motions of the patient. A particularly good technique is to use the three axis gyroscopes incorporated in sensors 30 and 34 to detect the angular rotation rate of the shank and thigh of patient 52 when they are moving and use this data to correct the readings taken from the accelerometers. In the preferred embodiment, a Kalman filter is used to make this correction.

The Kalman filter is an algorithm which uses a time series of measurements to estimate the next expected state of the system based on the current and previous states. It produces a statistically optimal estimate of the actual state of the system based on the measurements, even when the measurements include noise. In the case of an accelerometer and gyroscope, the accelerometer will include noise components as a result of motion, while the gyroscope will drift over time. In short, the accelerometer will give a good indication of the direction of gravity (hence the angle of the limb in question) over a long period of time, while the gyroscope will give a good indication of a change in angle over a short period of time, but will become increasingly inaccurate over longer periods of time due to drift. The Kalman filter thus uses both measurements to arrive at a good estimate of the actual orientation of the sensors.

In the preferred embodiment, readings are taken from sensors 30 and 34 every 1/10 of a second. The three acceleration measurements (X, Y and Z axes) and three gyroscope rate measurements (X, Y and Z axes) from sensor 30 are passed through the Kalman filter calculation to arrive at an estimate of the current X, Y and Z angles of sensor 30, which provides a vector representing the orientation of sensor 30 with respect to gravity. Similarly, the three acceleration measurements and three gyroscope rate measurements from sensor 34 are passed through the Kalman filter calculation to arrive at an estimate of the current X, Y and Z angles of sensor 34 with respect to gravity. As described above, the angle between the two resulting vectors is easily calculated.

The mathematics of a Kalman filter are well known in the art. In the preferred embodiment, the Kalman filter calculation is reduced to the following:

$$\text{Rate} = \text{NewRate} - \text{Bias} \quad 1)$$

Where temporary value Rate is calculated as the latest gyroscope rate reading (NewRate) minus the most recently calculated Bias amount. Bias is initially set to 0 and is updated during each pass through the Kalman filter.

$$\text{Angle} = \text{Angle} + \text{DeltaT} \times \text{Rate} \quad 2)$$

Where temporary value Angle is the previous value of Angle plus the time interval since the last reading (DeltaT) times the new Rate calculated in step 1.

$$P[0][0] = P[0][0] + \text{DeltaT} \times (\text{DeltaT} \times P[1][1] - P[0][1] - P[1][0]) + Q\_\text{angle}$$

$$P[0][1] = P[0][1] - \text{DeltaT} \times P[1][1]$$

$$P[1][0] = P[1][0] - \text{DeltaT} \times P[1][1]$$

$$P[1][1] = P[1][1] + \text{DeltaT} \times Q\_\text{bias} \quad 3)$$

Where P[ ][ ] is the covariance matrix, Q_angle and Q_bias are constants. This step updates the estimation error covariance.

$$K[0] = P[0][0]/(P[0][0] + R\_\text{Measure})$$

$$K[1] = P[1][0]/(P[0][0] + R\_\text{Measure}) \quad 4)$$

Where constant R_Measure is used to update the Kalman gain matrix K.

$$\text{tempAngle} = \text{newAngle} - \text{Angle} \quad 5)$$

$$\text{Angle} = \text{Angle} + K[0] \times \text{tempAngle} \quad 6)$$

$$\text{Bias} = \text{Bias} + K[1] \times \text{tempAngle} \quad 7)$$

In these steps, the angle calculated during that previous pass through the Kalman filer is subtracted from the new reading of the angle from the accelerometer, newAngle to get tempAngle, the change in angle. This is adjusted by the Kalman gain K[0] calculated in the previous step to arrive at a new value of the estimated actual angle, Angle. Similarly, a new value for Bias is calculated by multiplying the Kalman gain K[1] by tempAngle.

$$P[0][0] = P[0][0] - K[0] \times P[0][0]$$

$$P[0][1] = P[0][1] - K[0] \times P[0][1]$$

$$P[1][0] = P[1][0] - K[1] \times P[1][0]$$

$$P[1][1] = P[1][1] - K[1] \times P[1][1] \quad 8)$$

As a final step of the Kalman filter, the values of the covariance matrix are updated based on the updated Kalman gain.

It can been seen from the above that each of the X, Y and Z axis measurements of the inertial sensor (newAngle) can be combined with the X, Y and Z axis measurements of the gyroscope (NewRate) to arrive at a best estimate of the actual magnitude of gravitational acceleration measured by the sensors with respect to each axis. Doing this for the data read from both of sensors 30 and 34 results in the two vectors from which the angle between the shank and thigh of patient 52 can be calculated, as described above. The data comprises the number of flexions, the degree of flexion and the maximum and minimum amount of flexion of the affected joint. The maximum and minimum flex angle achieved during each flex is important for the assessment of the patient's rehabilitation because it is important to get the joint fully straight as part of the recovery process.

This angle information read from the sensors may be presented to the caregiver in many different forms, one of which is graphically, as hereinafter described.

Data from the two temperature sensors is also processed by database and server 20 to calculate the difference in temperature measured by temperature sensor 36 and temperature sensor 32. This difference in temperature is meaningful to the caregiver in that an elevation of the temperature measured by temperature sensor 32, which is located near surgical incision 54, with respect to the basal temperature measured by temperature sensor 36, which is located separated from the surgical incision 54 by a great enough distance that the sensor 36 will not detect an elevated temperature at the incision, may be indicative of infection of surgical incision 54. Alternatively, a decrease in the temperature measured by temperature sensor 32 with respect to the basal temperature measured by temperature sensor 36 is a good indication that the patient is applying ice to the surgical site, which is a desirable part of the rehabilitation protocol.

The absolute temperature measured by sensors 32 and 36 is also of clinical interest. A rise in basal temperature as measured by temperature sensor 36, which is removed a distance from surgical incision 54, could indicate body heating due to exercise in the case of a small temperature rise, or a system infection causing a fever in patient 52. Similarly, a fall in the absolute temperature of sensor 32 is likely indicative of icing of the knee joint. Therefore, although there are advantages to considering the temperature differences between sensors 32 and 36, either sensor can provide useful information by itself.

The duration of temperature measured by sensor 32 is of clinical value as well and is data that is collected and analyzed by the present invention. As an example, if the absolute temperature measured by sensor 32 is indicative of the patient icing the joint, then determining the time that the temperature is indicative of icing allows the caregiver to know how long the patient is icing the joint.

Data from stretch sensor 33 represents the girth of the patient's limb at the position of stretch sensor 33. In the described position, change of girth due to motion of the patient's leg (and underlying muscles) is minimized and can be averaged out over long time periods. The resulting average girth measurement is a useful indication of swelling of the patient's limb in response to infection or overuse.

Figure 5:
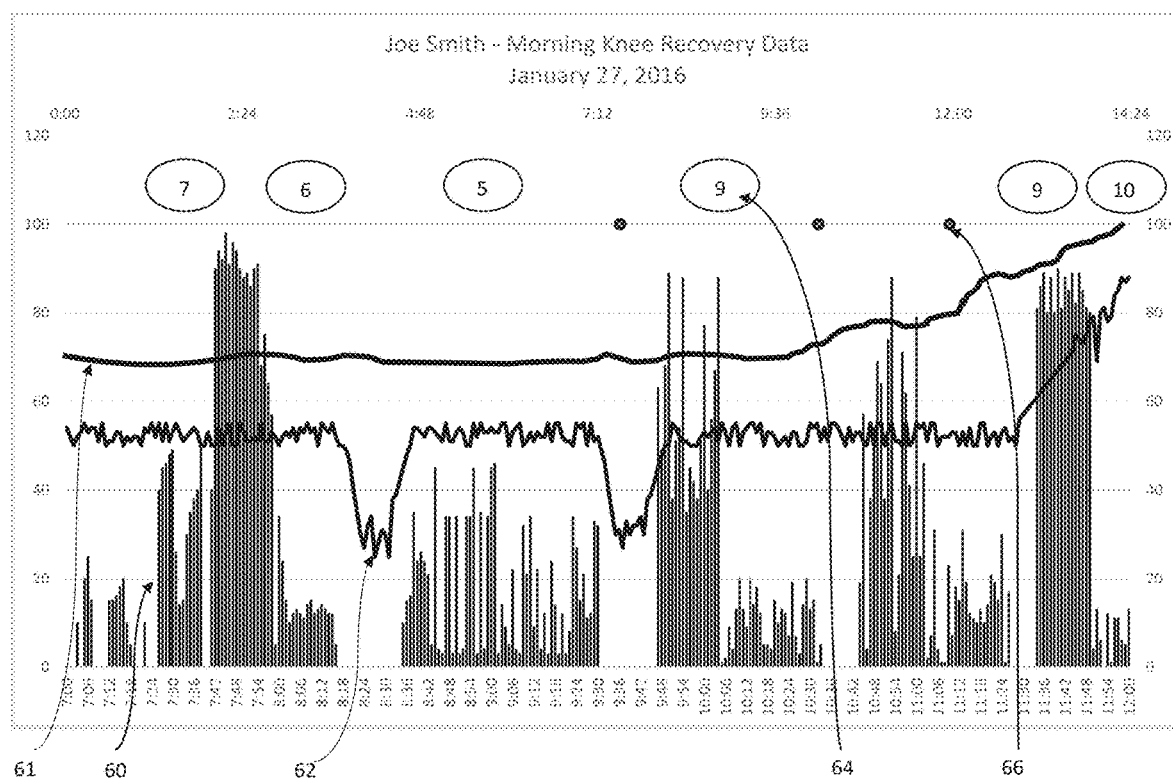
FIG. 5 is a graphical display of how data obtained from patient-worn sensors according the present invention may be displayed on, for example, a computer monitor.

FIG. 5 shows one of many possible ways to display the data obtained from patient worn sensors 10 as processed by database and server 20. In this graphical representation, vertical lines 60 indicate a knee flexion. The height of the line is proportional to the degree of flexion as indicated on the vertical axis. Thus a caregiver can easily determine the degree of activity, number of times the patient has flexed their knee and by what amount.

Line 62 shows the temperature difference between temperature sensors 32 and 36. In the figure, two periods of decreased temperature would indicate to the caregiver that the patient is properly icing their knee. To the right end of the temperature curve, there is a sharp and steady rise in the temperature difference. This would indicate to the caregiver the onset of infection. In this embodiment, the temperature differential is shown, however it is clear that similarly useful information can be conveyed by showing the absolute temperature measured by either or both sensors and the duration of time either or both of the sensors 32 and 36 remain at a given temperature or temperature range.

Line 61 shows the time averaged girth of the patient's limb as measured by stretch sensor 33. In the preferred embodiment, readings from analog to digital converter 31 are taken once every second and averaged over the previous 100 measurements, thus creating a time average that filters out relatively fast changes that are likely due to motion rather than swelling. As can be seen from line 61, the girth of the patient's limb (hence the amount of limb swelling) is relatively constant until it begins to rise at the right end of the graph. This would indicate to the caregiver that there is significant swelling of the limb.

As the connection between remote computer 24 is connected to local computer 16 via Internet connections 22 and 18 is bi-directional, it is possible for the caregiver to interact with patient 52 using email, text messaging, or video chat using any number of easily available Internet communications tools. In the preferred embodiment, this communications was facilitated using the Claris Companion Android app from Claris Healthcare Inc. (www.clariscompanion.com). The Claris Companion app was integrated with the database and server of the preferred embodiment to add additional useful information to the graphical display of data for the caregiver, as well as to provide additional useful functions. For example, the Claris Companion app is configured to allow patient 52 to voluntarily provide a "pain score" from 1-10, where 1 is no pain at all and 10 is excruciating. Pain scores 64 are displayed along the time axis in FIG. 5 so that the caregiver can correlate the pain score with activity or temperatures. In addition, the Claris Companion app is configured to report whenever the patient chooses to take pain medication, as indicated by marks 66 in FIG. 5.

In addition to the manual communication between the caregiver and patient 52 made possible by the present invention, the preferred embodiment provides automated coaching and encouragement to patient 52 via local computer 16. For example, the caregiver can set goals for patient 52 such as completing 25 repetitions of a knee flex beyond 80 degrees. When database and server 20 calculates that the target repetitions are completed by analyzing the data from patient worn sensors 10, it causes local computer 16 to display a congratulatory message. Similarly, analysis of the temperature data from patient worn sensors 10 can cause local computer 16 to show a confirmation message when patient 52 successfully lowers the temperature of surgical incision 54 by a desired amount, and can then start an on-screen timer to indicate how long the lowered temperature should be maintained. Further automated or manual coaching and encouragement can be provided in the form of instructional videos or photographs, encouraging messages, social interaction with similar patients, and 'gamification' in the form of goals, rewards and progress reporting.

Figure 6:
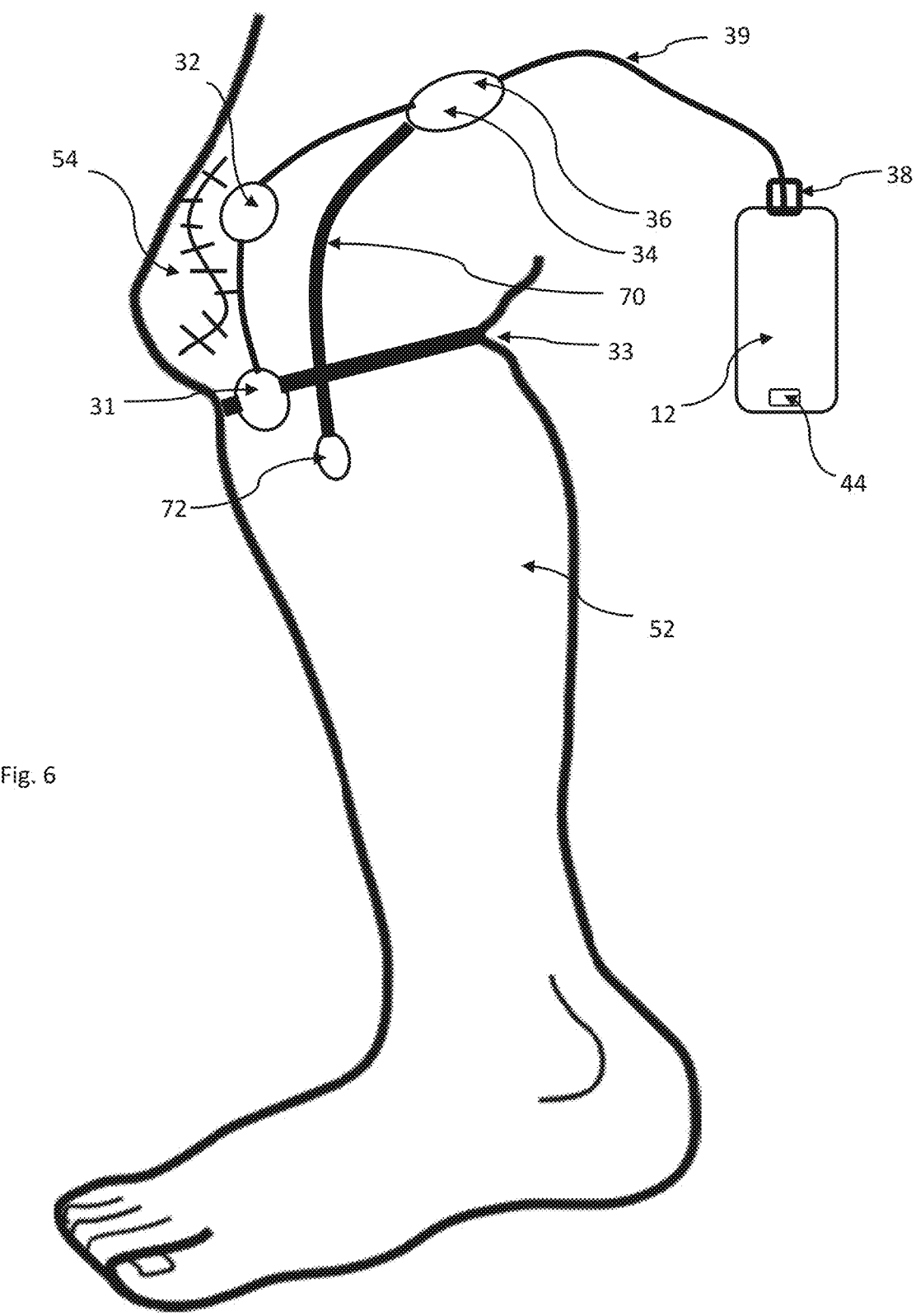
FIG. 6 is a schematic illustration analogous to FIG. 3, except illustrating an alternative embodiment of an apparatus for measuring the flexion of the patient's leg.

FIG. 6 illustrates an alternative sensing means for determining the degree of flexion of the knee of patient 52. In this embodiment, distal motion sensor 30 is replaced with capacitive flex sensor 70, which in the preferred embodiment is a Soft Silicon Bend Sensor (bendlabs.com) that provides a signal proportional to the angle of flexion of sensor 70. Flex sensor 70 is an elongate strip attached to the leg of patient 52 so that the strip extends above, over and below the knee joint using anchor 72 and the case that encloses sensors 36 and 34. As sensor 70 provides a signal directly proportional to the degree of flexion of the knee of patient 52, there is no need to perform mathematical calculations to determine the flexion angle. Although no longer used in the calculation of the flexion angle, motion sensor 34 is retained in order to allow the orientation of the thigh of patient 52 to be measured. Knowing this orientation allows a caregiver to determine the body position of patient 52 while they are flexing their knee. For example, should motion sensor 34 indicate that the thigh of patient 52 is horizontal while the knee is flexed, it would indicate that patient 52 is performing the exercise while sitting, while if motion sensor 34 indicates that the thigh of patient 52 is vertical, it would indicate that the exercise is being performed while standing. Thus, data corresponding to the orientation of the limb that is proximate to the joint relative to a ground plane (i.e., a horizontal reference plane) is an effective in monitoring rehabilitation therapy.

Figure 7:
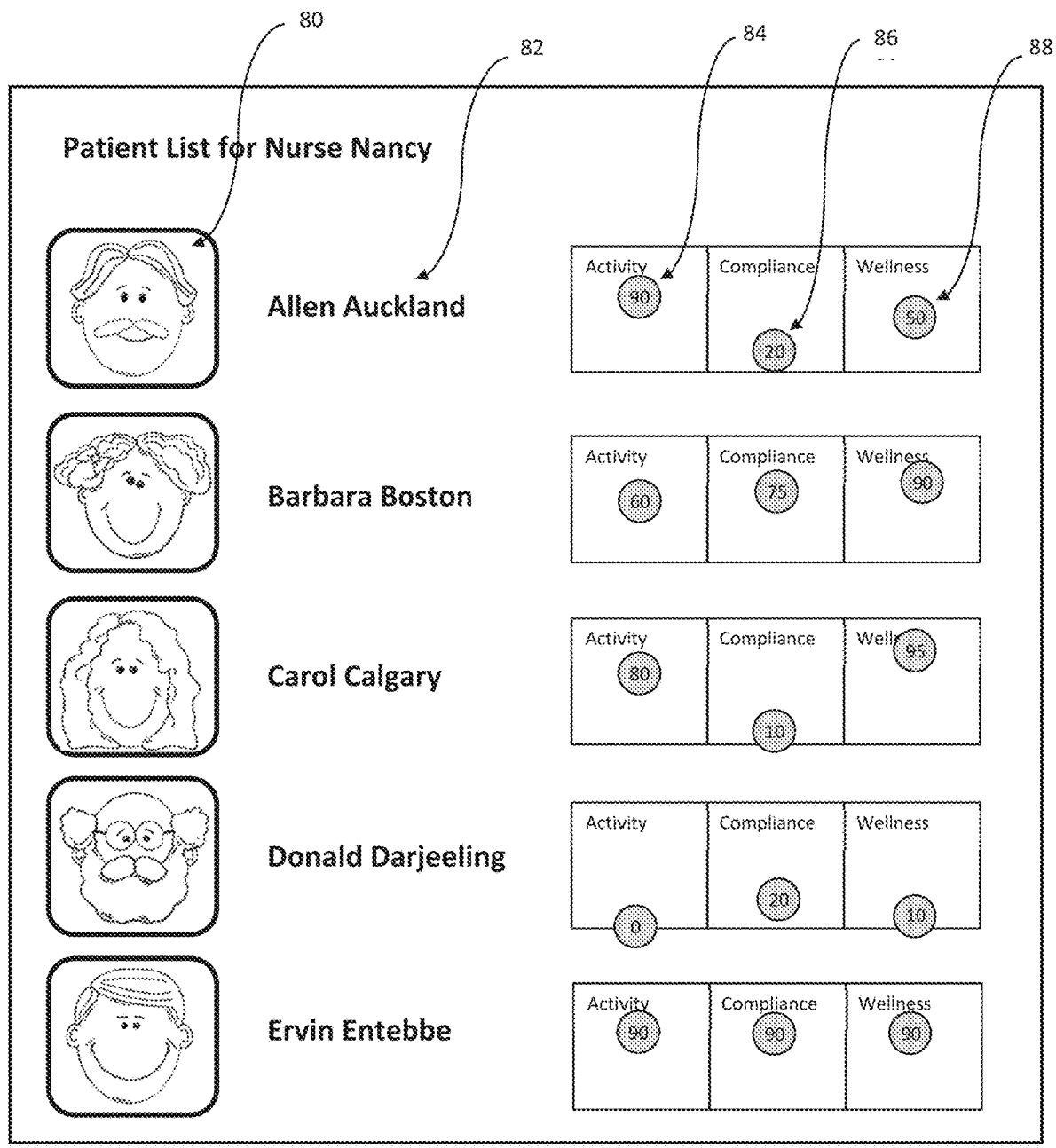
FIG. 7 is a schematic representation illustrating one preferred way that data generated according to the invention may be displayed to a caregiver who has responsibility for monitoring plural patients.

FIG. 7 illustrates another advantageous way to display the data obtained from patient worn sensors 10 as processed by database and server 20. This embodiment anticipates that a caregiver may be responsible for several patients simultaneously, thus is it helpful to be able to determine the status of selected and predetermined patient conditions for several patients in summary form without having to examine and interpret the detailed data as presented in the embodiment shown in FIG. 5. In the alternative embodiment shown in FIG. 7, each patient is represented by a row of information icons, including patient photo 80, patient name 82, Activity icon 84, Compliance icon 86 and Wellness icon 88. Each of Activity icon 84, Compliance icon 86 and Wellness icon 88 are labelled with a number representing, in the preferred embodiment, a score ranging from 0 to 100, calculated as hereinafter described. A further enhancement to rapid understanding of the relative score for each factor, not illustrated in FIG. 7, is that each of Activity icon 84, Compliance icon 86 and Wellness icon 88 display as a different color depending on the score: if the score is 33 or below, the icon is colored red; if between 34 and 66, the icon is colored yellow; while if the score is above 66, the icon is colored green. Thus a caregiver can quickly determine which of the patients in his or her charge are doing well and which are doing poorly.

The Activity score is calculated by combining data from several sources associated with the patient. One source of data is patient worn sensors 10. Data from sensors 10 are used to determine how often the patient has flexed their knee during the day and comparing that to a pre-determined ideal activity level for that time of day, or to previous days for the same patient, to arrive at a value representing a percentage of normal activity. An additional score is calculated based on the number of times the patient has interacted with local computer device 16, again compared to a pre-determined ideal activity level to arrive at a percentage of normal interaction frequency. Finally, data from patient worn sensors 10 is used to determine the total period of time the patient has been moving and the total period of time the patient has been stationary, and to calculate a third activity score representing the percentage of time the patient is moving. The three scores are weighted and combined into a total activity score; in the preferred embodiment, the score representing knee flexes is weighted at 70%, the interactions with local computer device 16 are weighted at 20% and the percentage of time moving is weighted at 10%, thereby deriving an activity score between 0 and 100. Each time the Activity score is calculated, the number displayed in Activity icon 84 is updated, Activity icon 84 is moved up or down in the display area, and the color of the icon is changed if merited by the score.

The Compliance score is calculated by determining what percentage of prescribed activities the patient has completed, and how quickly they have completed them. For example, during the course of a day, the patient may be reminded to ice their knee five times at two hour intervals, be asked (via local computer device 16) to report their current pain scale, reminded to perform certain exercises, or be reminded to take medications. Compliance with these prescribed activities is determined from two sources—patient worn sensors 10 and the patient's interaction with local computer device 16. For example, sensors 10 will detect a decrease in temperature if and when the patient responds to a reminder to ice their knee, which would indicate compliance. Similarly, sensors 10 will detect appropriate motions if and when the patient complies with a reminder to do exercises. For other reminders, such as reporting pain scale or taking medications, the patient's response via local computer device 16 will indicate compliance, or the patient's election to skip the activity reminded. The compliance score displayed by Compliance icon 86 is calculated as follows: each time an activity reminder is displayed on local computer device 16, that activity is given a score of 100. For each pre-determined time period that elapses without the activity being completed, typically 5 minutes, one point is deducted from the score for this activity. Once the activity is completed, the resulting discounted score is recorded. At periodic intervals, the average score for all activities completed so far during the day is calculated. This becomes the revised Activity score, which is used to update the number appearing in Activity icon 86 and to adjust the position and color of Activity icon 86 on the caregiver's display.

The Wellness score is similarly calculated by combining data from patient worn sensors 10 and the patient's interaction with local computer device 16. In the case of wellness, the patient's response to a pain scale self-evaluation is given a high weighting. At regular intervals during their recovery, local computing device 16 displays a message asking the patient to rate their pain on a scale of 1 to 10, where 1 is very little pain and 10 is excruciating to thereby generate a pain score. This scale is inverted to calculate wellness, wherein a pain scale of 1 becomes a pain score of 100 and a pain score of 10 becomes a pain score of 0. Added to this is a temperature score, wherein, if the temperature recorded by sensors 10 is higher than a pre-determined normal temperature, the temperature score declines from 100 to 0 in proportion to the increased temperature. Finally, a swelling score is calculated in which the current girth of the limb is compared to the initial girth of the limb to determine a degree of swelling. If the measured girth is greater than the initial girth, the swelling score is discounted from 100 to 0 in proportion to the increase in girth. At periodic intervals, the total Wellness score is calculated by weighting the pain score at 80%, the temperature score at 10% and the swelling score at 10% to arrive at a total Wellness score ranging from 0 to 100. This becomes the revised Wellness score, which is used to update the number appearing in Wellness icon 88 and to adjust the position and color of Wellness icon 88 on the caregiver's display.

It will be evident based on the foregoing description and from the drawings that the present invention defines a method monitoring a patient and assessing the patient's condition by attaching a sensor to the patient for measuring a defined patient parameter, recording patient parameter data from the sensor, providing an input device to the patient and prompting the patient to enter patient input data into the input device, recording the patient input data; and assigning a score that is indicative of the patient parameter by combining the first patient parameter data and patient input data. As detailed, plural sensors may be used for monitoring different patient parameters such as flexion, temperature and swelling and the method is useful for generating status scores that quickly provide a caregiver with a way to assess the patient's condition in relation to the different patient parameters, including Activity, Compliance and Wellness. The methods further enable a patient's compliance with a rehabilitation regimen that has been prescribed for the patient, including prompting the patient to enter patient input data into the input device, the patient input data correlating to a desired patient condition, recording the time of the prompt, recording the patient input data entered by the patient and the time that the patient input data are entered by the patient, determining the time between when the patient is prompted and the time when the patient enters the patient input data, and generating a patient compliance score from the time between when the patient is prompted when the patient enters the patient input data, the patient compliance score providing a measure of the patient's compliance with a treatment regimen for the desired patient condition.

Many variations on the preferred embodiment described here can be easily imagined. For example, although the invention as herein described is shown as used for a knee joint, it can easily be extended to operate in a similar fashion for any other joint on which surgery may be performed. The sensors described are one choice of many possibilities for measuring joint motion and temperature, and the choice of a data logger with local memory and periodic uploading could be eliminated in favour of real-time transfer of data from sensors 10 to local computer 16. Furthermore, it is possible to eliminate the cable and I2C bus by having each sensor connected to a separate Bluetooth radio linked to the local computer. It is also clear that there are other mathematical techniques for filtering data from accelerometers and gyroscopes to improve their accuracy and extracting the angle between sensors 30 and 34, many of which could provide equally useful measurements.

Based on review of the foregoing disclosure and the drawings, it should also be evident to one skilled in the art that there are many equivalent ways to calculate Activity, Compliance and Wellness scores, or other scores of interest to caregivers, and to display the value of such scores graphically to allow a caregiver to quickly evaluate a number of patients. Further, the weighting given to the various data sources used to determine such scores can obviously be changed to reflect the relative importance of each data source with respect to the patient's condition.

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

The invention claimed is:
1. Apparatus for monitoring a patient, comprising:
 a first motion sensor adapted to be attached to a patient's limb distally of a joint;
 a first temperature sensor adapted to be attached to the patient's limb in proximity to a surgical site;
 a second motion sensor adapted to be attached to the patient's limb proximately of the joint;

a second temperature sensor adapted to be attached to the patient's limb proximate the joint and the spaced from the first temperature sensor;

wherein the first and second motion sensors are configured for generating limb orientation data and transmitting the limb orientation data to a microprocessor that includes memory to store the limb orientation data and execute instructions thereupon, and to thereby generate a representation of the orientation of the patient's limb distal of the joint and the patient's limb proximate of the joint over time and to thereby count the number of flexions of the joint;

a patient-assigned computer;

wherein the microprocessor is configured to generate an activity score by
a. using limb orientation data to determine the number of flexions and compare the number of flexions to a predetermined ideal number of flexions and to calculate a percentage of normal activity;
b. determining the number of times the patient has interacted with the patient-assigned computer to calculate a percentage of normal interaction frequency;
c. using limb orientation data to calculate the percentage of time the patient is moving; and
d. weighting the percentage of normal activity, the percentage of normal interaction frequency, and the percentage of time the patient is moving to derive the activity score.

2. The apparatus according to claim 1 in which the limb orientation data further comprises the maximum and minimum flex angle of each flexion.

3. The apparatus according to claim 1 wherein the first and second temperature sensors are configured for generating temperature data and transmitting the temperature data to the microprocessor for comparison of the temperature data from the first temperature sensor with the temperature data from the second temperature sensor and thereby determine the difference in temperature data between the first and second temperature sensors.

4. The apparatus according to claim 3 in which the difference in temperature data between the first and second temperature sensors is indicative of infection at the surgical site.

5. The apparatus according to claim 3 in which the difference in temperature data between the first and second temperature sensors is indicative of icing at the surgical site.

6. The apparatus according to claim 1 further comprising calculating the percentage of normal interaction frequency by determining the number of times the patient has interacted with the patient-assigned computer and comparing that to a predetermined ideal number of interactions.

7. The apparatus according to claim 1 in which the activity score is calculated by weighting the percentage of normal activity at 70 percent, the percentage of normal interactions at 20 percent, and the percentage of time the patient is moving at 10 percent.

8. The apparatus according to claim 1 wherein the microprocessor is configured to generate a compliance score between 0 and 100 by
a. prescribing a number of activities for the patient;
b. using data from the patient-assigned computer, determining the number of activities the patent has completed within a predetermined time; and
c. comparing the number of prescribed activities to the number activities the patent has completed.

9. The apparatus according to claim 1 wherein the microprocessor is configures to generate a wellness score between 0 and 100.

10. Apparatus for monitoring a patient, comprising:
a first motion sensor adapted to be attached to a patient's limb distally of a joint;
a first temperature sensor adapted to be attached to the patient's limb in proximity to a surgical site;
a second motion sensor adapted to be attached to the patient's limb proximately of the joint;
a second temperature sensor adapted to be attached to the patient's limb proximate the joint and the spaced from the first temperature sensor;
wherein the first and second motion sensors are configured for generating limb orientation data and transmitting the limb orientation data to a microprocessor that includes memory to store the limb orientation data and execute instructions thereupon, and to thereby generate a vector representation of the orientation of the patient's limb distal of the joint and the patient's limb proximate of the joint over time and to thereby count the number of flexions of the joint;
wherein the first and second temperature sensors are configured for generating temperature data and transmitting the temperature data to the microprocessor for comparison of the temperature data from the first temperature sensor with the temperature data from the second temperature sensor and thereby determine the difference in temperature data between the first and second temperature sensors;
a patient-assigned computer in communication with the microprocessor to transmit patient-input data to the microprocessor;
wherein, the microprocessor generates at least one score from the limb orientation data, temperature data or patient-input data.

11. The apparatus according to claim 10 in which the difference in temperature data between the first and second temperature sensors is indicative of infection at the surgical site.

12. The apparatus according to claim 10 in which the difference in temperature data between the first and second temperature sensors is indicative of icing at the surgical site.

13. The apparatus according to claim 10 in which the temperature data includes the duration of time for temperature data from the first temperature sensor.

14. The apparatus according to claim 10 in which the temperature data includes the duration of time for temperature data from the second temperature sensor.

15. The apparatus according to claim 10 in which the temperature data from the first and second temperature sensors is compared to a pre-determined normal temperature to generate a temperature score.

16. A method of monitoring a patient's recovery from surgery on a limb, comprising the steps of:
a. attaching a first motion sensor adapted to a patient's limb distally of a joint;
b. attaching a first temperature sensor to the patient's limb in proximity to a surgical site;
c. attaching a second motion sensor to the patient's limb proximately of the joint;
d. attaching a second temperature sensor to the patient's limb proximate the joint and the spaced from the first temperature sensor;
e. attaching a stretch sensor to the patient's limb proximate the joint;

f. from the first and second motion sensors, generating limb orientation data and transmitting the limb orientation data to a microprocessor that includes memory to store the limb orientation data and execute instructions thereupon, and to thereby generate a representation of the orientation of the patient's limb distal of the joint and the patient's limb proximate of the joint over time and to thereby count the number of flexions of the joint;

g. from the first and second temperature sensors, generating temperature data and transmitting the temperature data to the microprocessor and comparing the temperature data from the first temperature sensor with the temperature data from the second temperature sensor and thereby determine the difference in temperature data between the first and second temperature sensors to thereby generate a temperature score;

h. from the stretch sensor, generating limb girth data limb and transmitting the limb girth data to the microprocessor to thereby generate a swelling score representation of the girth of the patient's limb; and i. assigning to the patient a computer and prompting the patient to input into the computer pain data, and transmitting the pain data to the microprocessor to generate a pain score;

j. from pain score, temperature score and swelling score, calculating a wellness score indicative of the patient's condition.

17. The method according to claim 16 including for each flexion of the patient's joint the step of comparing the angle of flexion to a pre-determined angle of flexion.

18. The method according to claim 16 including the step of determining if the determined difference in temperature data between the first and second temperature sensors is indicative of infection.

19. The method according to claim 16 including the step of including the step of determining if the determined difference in temperature data between the first and second temperature sensors is indicative of icing.

20. The method according to claim 16 including the step of determining if the limb girth data is indicative of swelling.

* * * * *